(12) United States Patent
McKeeman

(10) Patent No.: US 11,052,007 B2
(45) Date of Patent: Jul. 6, 2021

(54) SYSTEM FOR COOLING A PRESSURIZED HYPERBARIC CHAMBER WITHOUT PRESSURE CHANGE

(71) Applicant: Bruce Elgin McKeeman, Mound, MN (US)

(72) Inventor: Bruce Elgin McKeeman, Mound, MN (US)

(*) Notice: Subject to any disclaimer, the term of this patent is extended or adjusted under 35 U.S.C. 154(b) by 600 days.

(21) Appl. No.: 15/890,134

(22) Filed: Feb. 6, 2018

(65) Prior Publication Data
US 2019/0240097 A1 Aug. 8, 2019

(51) Int. Cl.
*A61G 10/02* (2006.01)
*F24F 13/02* (2006.01)
*F24F 5/00* (2006.01)

(52) U.S. Cl.
CPC .......... *A61G 10/026* (2013.01); *F24F 5/0085* (2013.01); *F24F 13/0209* (2013.01); *A61M 2202/0208* (2013.01)

(58) Field of Classification Search
CPC ..... A61G 10/023; A61G 10/026; F24F 5/008; F24F 5/0085
See application file for complete search history.

(56) References Cited

U.S. PATENT DOCUMENTS

| | | | | |
|---|---|---|---|---|
| 2,342,299 A * | 2/1944 | Peet | ..................... | B67D 1/0867 62/390 |
| 4,296,743 A * | 10/1981 | Lasley | ................. | A61G 10/026 600/21 |
| 5,327,904 A * | 7/1994 | Hannum | ............... | A61G 10/026 128/202.12 |
| 5,618,126 A * | 4/1997 | Watt | ..................... | A61G 10/026 294/68.1 |
| 6,016,803 A * | 1/2000 | Volberg | ............... | A61G 10/026 128/202.12 |
| 6,325,137 B1 * | 12/2001 | Elliott | ................... | F24F 5/0017 165/122 |
| 8,251,057 B2 * | 8/2012 | Butler | .................. | B63C 11/325 128/202.12 |
| 9,622,931 B2 | 4/2017 | McKeeman | | |
| 9,664,202 B2 | 5/2017 | McKeeman | | |
| 2004/0261796 A1 * | 12/2004 | Butler | .................. | A61G 10/026 128/205.26 |
| 2008/0210234 A1 * | 9/2008 | O'Brien | ............... | A61G 10/026 128/202.12 |

(Continued)

*Primary Examiner* — LaToya M Louis

(57) ABSTRACT

A system for cooling a pressurized hyperbaric chamber without pressure change includes an air compressing unit, an air cooling unit, and an air discharging hose. The pressurized hyperbaric chamber, the air compressing unit, the air cooling unit, and the air discharging hose are in fluid communication with each other. A flow of output warm air from the pressurized hyperbaric chamber is withdrawn and discharged into the air cooling unit by the air compressing unit. A heat exchanger of the air cooling unit then removes heat energy from the flow of output warm air to convert the flow of output warm air into a flow of input cold air, as the heat exchanger is in fluid communication with stored ice water within an insulated reservoir of the air cooling unit. The flow of input cold air is then discharged back into the pressurized hyperbaric chamber through the air discharging hose.

10 Claims, 7 Drawing Sheets

(56) References Cited

U.S. PATENT DOCUMENTS

2008/0210239 A1\* 9/2008 Lewis ................... A62B 31/00
128/205.26
2008/0213825 A1\* 9/2008 Verri Lima .......... A01N 1/0257
435/41

\* cited by examiner

SYSTEM FOR COOLING A PRESSURIZED HYPERBARIC CHAMBER WITHOUT PRESSURE CHANGE

FIELD OF THE INVENTION

The present invention relates generally to a system for cooling a pressurized hyperbaric chamber without pressure change. More specifically, the present invention utilizes a compressor, an air cooling unit, and an air discharging hose in order to converts a flow of output warm air from a pressurized hyperbaric chamber into a flow of input cold air without changing the pressure within the pressurized hyperbaric chamber.

BACKGROUND OF THE INVENTION

Hyperbaric chambers are commonly used in the fields of diving and hyperbaric medicine. Hyperbaric chambers are pressurized vessels designed for human occupancy, and can be designed with either a soft or hard-shelled construction. The act of pressurizing air within a hyperbaric chamber generates heat within the enclosed environment of the hyperbaric chamber. As a result, a hyperbaric chamber without a cooling system results in a very hot and uncomfortable environment.

To overcome generated heat within hyperbaric chambers, many systems include some sort of cooling systems. The cooling systems utilize various methods and equipment, including chillers and chlorofluorocarbon based coolers, such as Freon to moderate the temperature within the hyperbaric chambers thus cooling the input air flow to comfortable levels for occupants. However, these methods and equipment have many drawbacks as they reduce the efficiency of the hyperbaric chambers. For examples, chillers have issues with condensation and mold, and tend to be high maintenance. Chlorofluorocarbon based coolers have no sound reducing qualities and have potentially harmful effects on certain individuals and the environment. In other words, these existing cooling solutions have some combination of downside such as loudness, unsanitary, hazardous, and difficult to maintain.

It is therefore an object of the present invention to provide a system for cooling a pressurized hyperbaric chamber without pressure change. More specifically, the present invention accomplishes this by arranging an air compressing unit, an air cooling unit, and an air discharging hose so that a flow of output warm air from the pressurized hyperbaric chamber can be recycled and converted into a flow of input cold air. Resultantly, the pressurized hyperbaric chamber can maintain a comfortable environment for the users through the present invention.

DETAIL DESCRIPTIONS OF THE INVENTION

Figure 1:
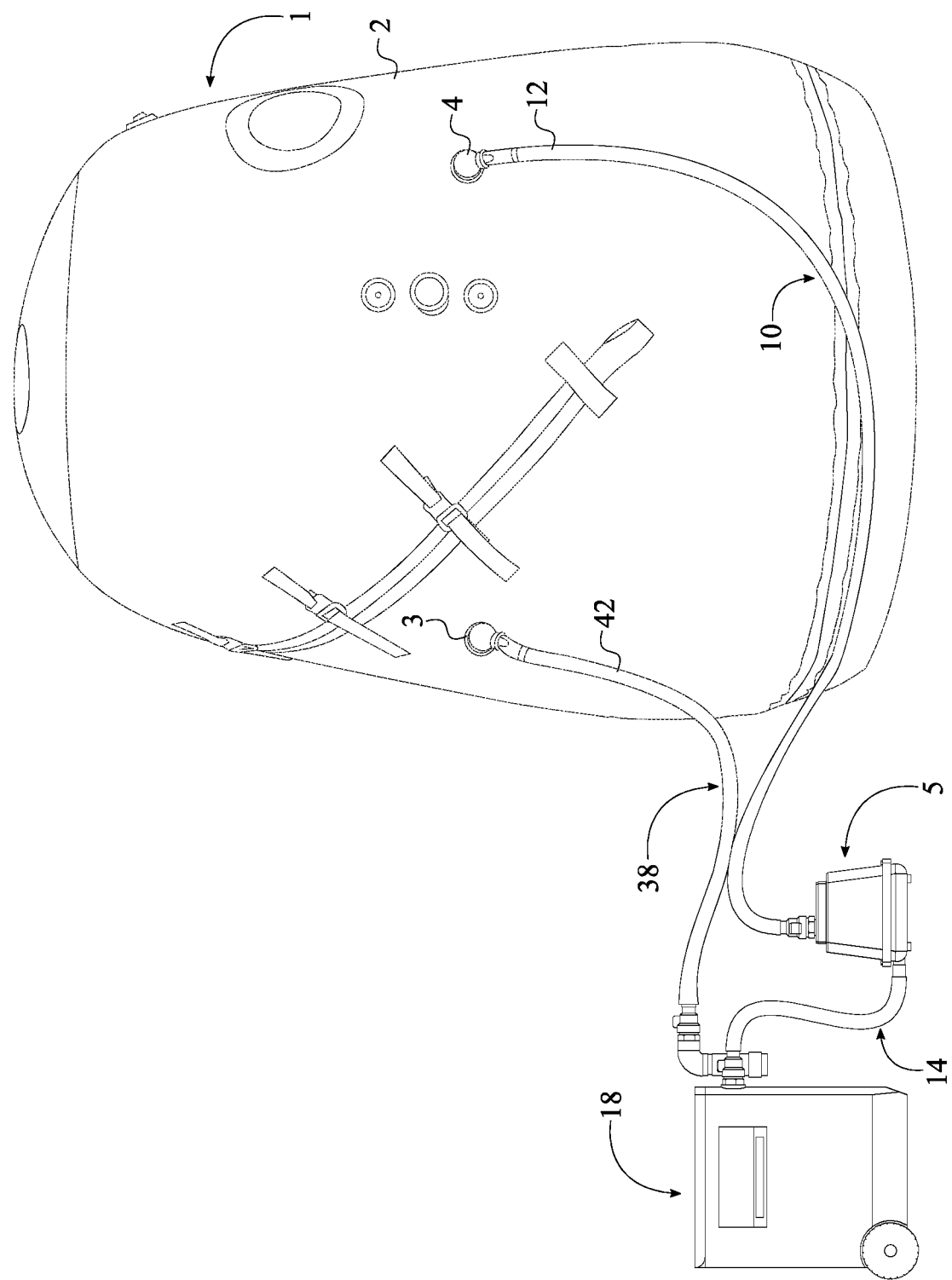
FIG. 1 is a side perspective view of the present invention.

All illustrations of the drawings are for the purpose of describing selected versions of the present invention and are not intended to limit the scope of the present invention.

The preset invention is a system for cooling a pressurized hyperbaric chamber 1 without pressure change within the pressurized hyperbaric chamber 1. More specifically, the present invention removes a flow of output warm air from the pressurized hyperbaric chamber 1 and converts the flow of output warm air into a flow of input cold air so that the pressurized hyperbaric chamber 1 can withstand as a pressurized enclosure without experiencing any pressure change. In reference to FIG. 1, the present invention comprises an air compressing unit 5, an air cooling unit 18, and an air discharging hose 38 in order to convert the flow of output warm air into the flow of input cold air.

In reference to the general configuration of the present invention, the air compressing unit 5 draws the flow of output warm air from the pressurized hyperbaric chamber 1 and discharges into the air cooling unit 18 so that the flow of output warm air can be converted into the flow of input cold air. The air cooling unit 18 comprises an insulated reservoir 19, a male reservoir inlet 20, a reservoir outlet 21, a heat exchanger 24, and a submersible pump 29. More specifically, the male reservoir inlet 20 and the reservoir outlet 21 traverse into the insulated reservoir 19. The heat exchanger 24 and the submersible pump 29 are positioned within the insulated cooler. In reference to FIG. 1-3, the pressurized hyperbaric chamber 1 is in fluid communication with the air compressing unit 5 so that the flow of output warm air can be withdrawn from the pressurized hyperbaric chamber 1. An air inlet 25 of the heat exchanger 24 is in fluid communication with the air compressing unit 5 through the male reservoir inlet 20 thus allowing the flow of output warm air to be discharged into the heat exchanger 24. A water outlet 28 of the heat exchanger 24 is in fluid communication with a water inlet 26 of the heat exchanger 24 through the submersible pump 29 as the water inlet 26 is connected to the submersible pump 29. The insulated reservoir 19 is filled with a quantity of ice water, and the submersible pump 29 supplies a flow of ice water into the heat exchanger 24 from the quantity of ice water. Resultantly, the flow of ice water is able to withdraw thermal energy from the flow of output warm air within the heat exchanger 24 thus completing the heat transfer process from the flow of output warm air to the quantity of ice water. More specifically, the flow of ice water and the flow of output warm air travel in opposite directions within the heat exchanger 24 in order to maximize the efficiency of the heat transfer process. Then, the present invention is able to convert the flow of output warm air into the flow of input cold air. The flow of input cold air is then discharged into the pressurized hyperbaric chamber 1 through the air discharging hose 38 as an air outlet 27 of the heat exchanger 24 is in fluid communication with the air discharging hose 38 through the reservoir outlet 21. Due to the constant withdrawal of the flow of output warm air, the flow of input cold air can be discharged back into the pressurized hyperbaric chamber 1 thus maintaining a comfortable environment and constant pressure within the pressurized hyperbaric chamber 1.

In reference to FIG. 1, the pressurized hyperbaric chamber 1 comprises a chamber body 2, an inlet male attachment 3, and an outlet male attachment 4. The pressurized hyperbaric chamber 1 is a pressurized vessel which creates a controlled environment so that patients can rest during the medical treatments. The pressurized hyperbaric chamber 1 is preferably made into a cylindrical shape, but is not limited only to the cylindrical shape and can be any other geometrical shapes. An access opening that is positioned along the chamber body 2 provides an opening so that the patients can move in and out of the pressurized hyperbaric chamber 1. The access opening is hermetically sealed by a fastening mechanism during the operation of the present invention so that the pressurized air can be collected within the chamber body 2. For safety purposes, the fastening mechanism can be opened or closed from the inside of the chamber body 2 or the outside of the chamber body 2. The inlet male attachment 3 and the outlet male attachment 4 traverse into the chamber body 2 and are in fluid communication with the chamber body 2. More specifically, the inlet male attachment 3 supplies the flow of input cold air into the chamber body 2. The outlet male attachment 4 withdraws the flow of output warm air from the chamber body 2. The pressurized hyperbaric chamber 1 is pressurized by an air pressurization unit that functions as a standalone compressing unit so that the pressurized hyperbaric chamber 1 can be pressurized with compressed air. Additionally, the pressurized hyperbaric chamber 1 may comprise at least one pressure relief valve, a dump valve, a pressure gauge, and at least one auxiliary valve to optimize the functionality of the pressurized hyperbaric chamber 1 according to the patient's preference.

The air compressing unit 5 must be a sealed unit that is capable to drawing the flow of output warm air from the pressurized hyperbaric chamber 1 and blowing withdrawn warm air back into the air cooling unit 18. As a result, the air compressing unit 5 maintains constant pressure within the pressurized hyperbaric chamber 1. In reference to FIG. 1-3, the air compressing unit 5 comprises a compressor 6, an input hose 10, and an output hose 14. The compressor 6 comprises a compressor body 7, a male air inlet 8, and a compressed air outlet 9. More specifically, the male air inlet 8 and the compressed air outlet 9 are in fluid communication with each other through the compressor body 7 so that the air compressing unit 5 is able to withdraw the flow of output warm air through the male air inlet 8 and discharge the flow of output warm air through the compressed air outlet 9 as a flow of compressed warm air. The air compressing unit 5 has to be electrically powered within the present invention to operate the air cooling unit 18.

Figure 4:
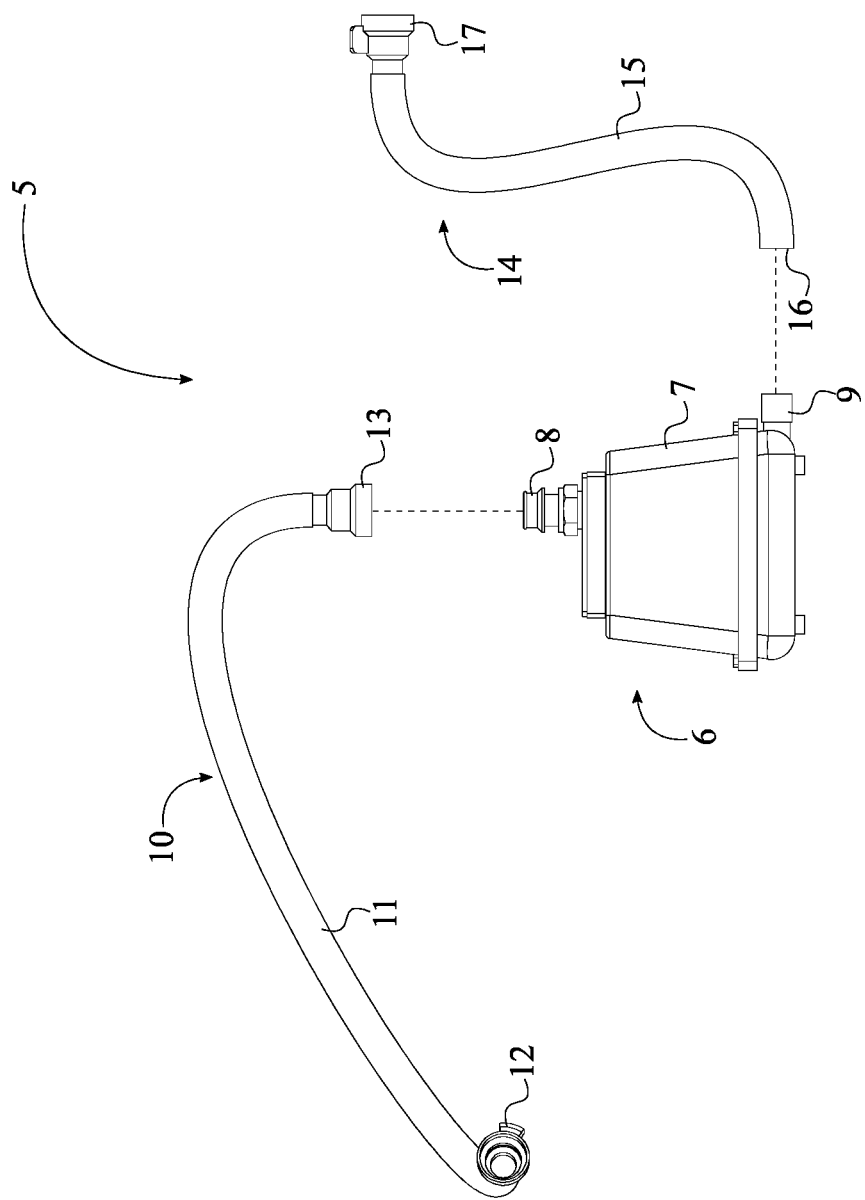
FIG. 4 is a side exploded view of the air compressing unit of the present invention.

In reference to FIG. 4, the outlet male attachment 4 of the pressurized hyperbaric chamber 1 and the male air inlet 8 are hermetically and releasably attached to each other by the input hose 10 and is in fluid communication with each other by the input hose 10. More specifically, the input hose 10 comprises a first hose body 11, a first female quick connector 12, and a second female quick connector 13. The first female quick connector 12 is terminally mounted to the first hose body 11 that is preferably made from flexible medical grade polyvinyl chloride (PVC) or any other type of flexible biocompatible materials. The second female quick connector 13 is terminally mounted to the first hose body 11, opposite of the first female quick connector 12. In other words, the first female quick connector 12 and the second female quick connector 13 are oppositely positioned of each other along the first hose body 11. Additionally, the first female quick connector 12 and the second female quick connector 13 are in fluid communication with each other through the first hose body 11 thus providing a path for the flow of output warm air to travel. In reference to the connection points, the first female quick connector 12 is attached to the outlet male attachment 4 of the pressurized hyperbaric chamber 1, and the second female quick connector 13 is attached to the male air inlet 8. Resultantly, the flow of output warm air is respectively withdrawn from the outlet male attachment 4 of the pressurized hyperbaric chamber 1 to the male air inlet 8 through the first female quick connector 12, the first hose body 11, and the second female quick connector 13.

In reference to FIG. 4, the compressed air outlet 9 and the male reservoir inlet 20 are hermetically and releasably attached to each other by the output hose 14 and are in fluid communication with each other by the output hose 14. More specifically, the output hose 14 comprises a second hose body 15, a first attachment opening 16, and a third female quick connector 17. The first attachment opening 16 is terminally positioned within the second hose body 15 that is preferably made from flexible medical grade PVC or any other type of flexible biocompatible materials. The third female quick connector 17 is terminally mounted to the second hose body 15, opposite of the first attachment opening 16. In other words, the first attachment opening 16 and the third female quick connector 17 are oppositely positioned of each other along the second hose body 15. Additionally, the first attachment opening 16 and the third female quick connector 17 are in fluid communication with each other through the second hose body 15 thus providing a path for the flow of compressed warm air to travel. In reference to the connection points, the first attachment opening 16 is mounted to the compressed air outlet 9, and the third female quick connector 17 is attached to the male reservoir inlet 20. Resultantly, the flow of compressed warm air is respectively discharged from the compressed air outlet 9 to the male reservoir inlet 20 through the first attachment opening 16, the second hose body 15, and the third female quick connector 17.

The air cooling unit 18 completely eliminates existing cooling methods such as the chillers and chlorofluorocarbon based coolers and their respective disadvantages. The chillers normally create condensation and mold problems over time while the chlorofluorocarbon based coolers are hazardous for certain individuals and environment. Since the air cooling unit 18 uses the quantity of ice water to withdraw thermal energy from the flow of output warm air, the submersible pump 29 has to be electrically powered within the present invention to operate the air cooling unit 18. In reference to FIG. 5, the air cooling unit 18 further comprises an inlet connector hose 30, an outlet connector hose 34, a male air outlet 22, and a condensate drain outlet 23 so that the flow of output warm air can be converted into the flow of input cold air within the air cooling unit 18. More specifically, the inlet connector hose 30 and the outlet connector hose 34 are positioned within the insulated reservoir 19. The male air outlet 22 and the condensate drain outlet 23 are positioned external to the insulated reservoir 19 and are connected to the reservoir outlet 21.

Figure 5:
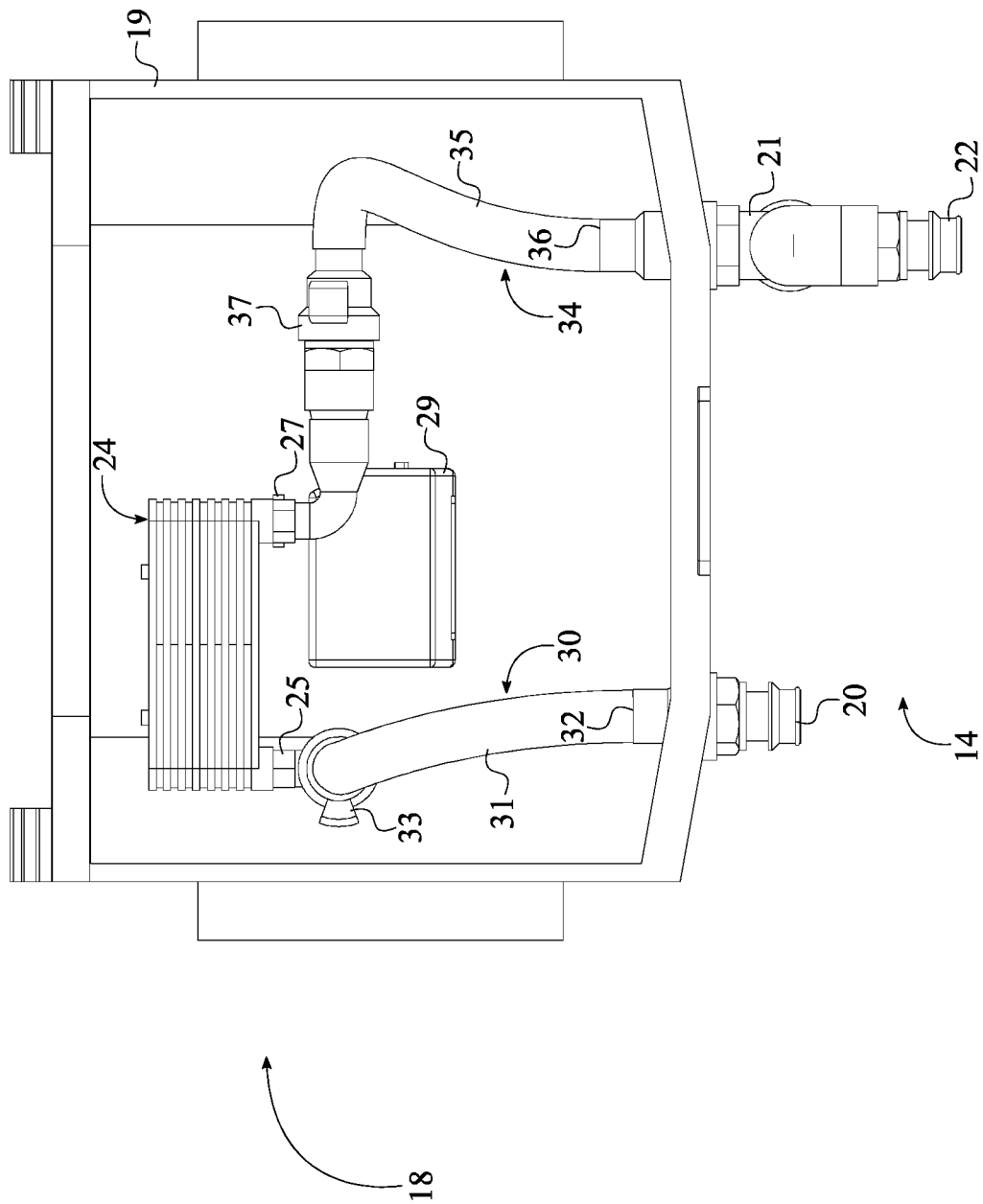
FIG. 5 is a top view of the air cooling unit of the present invention.

In reference to FIG. 5, the air inlet 25 is hermetically and releasably attached to the male reservoir inlet 20 by the inlet connector hose 30, as the air inlet 25 and the male reservoir inlet 20 are in fluid communication with each other by the inlet connector hose 30. As a result, the flow of compressed warm air that is emitted through the output hose 14 is discharged into the air inlet 25 through the male reservoir inlet 20 and the inlet connector hose 30.

Figure 6:
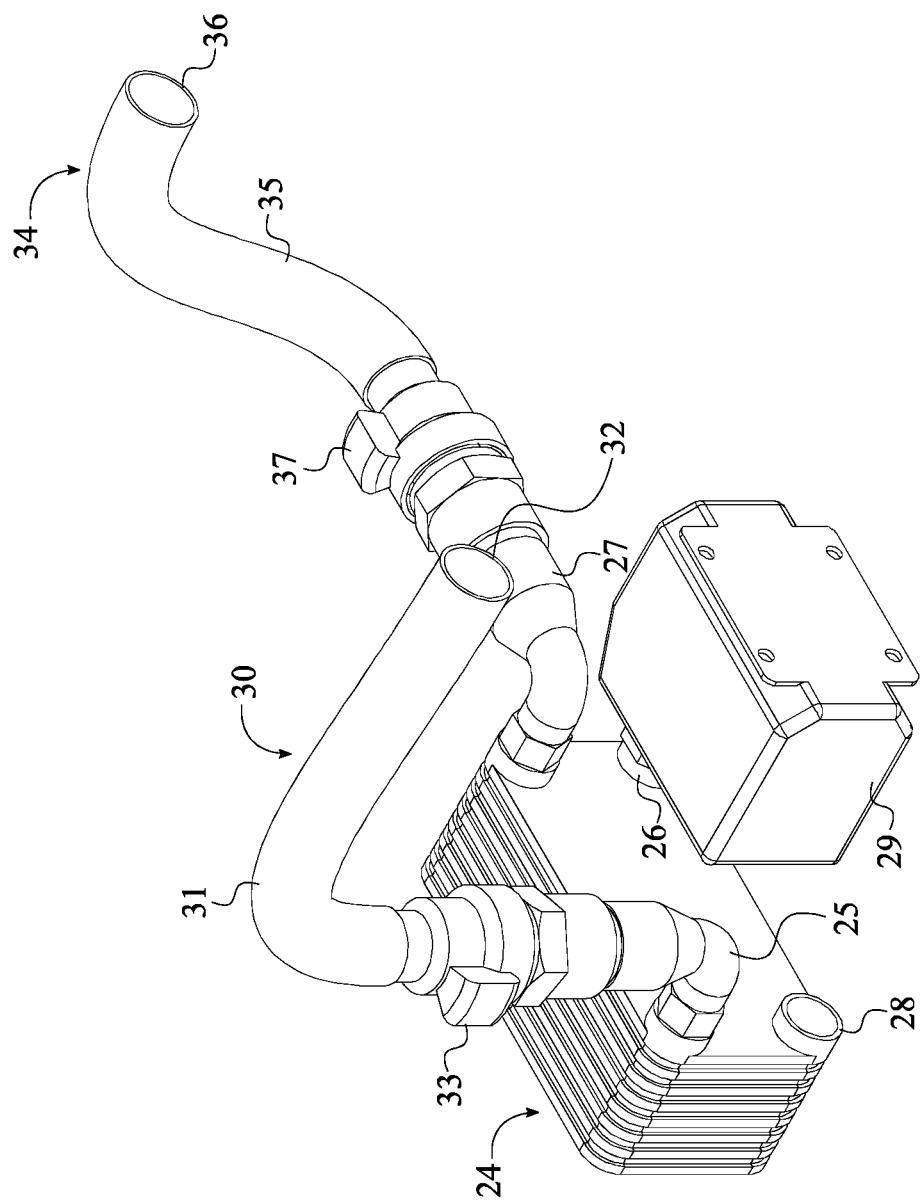
FIG. 6 is a perspective view of the heat exchanger, inlet connector hose, and the outlet connector hose of the present invention.

In reference to FIG. 5-6, the inlet connector hose 30 comprises a third hose body 31, a second attachment opening 32, and a fourth female quick connector 33. The second attachment opening 32 is terminally positioned within the third hose body 31 that is preferably made from flexible medical grade PVC or any other type of flexible biocompatible materials. The fourth female quick connector 33 is terminally mounted to the third hose body 31, opposite of the second attachment opening 32. In other words, the second attachment opening 32 and the fourth female quick connector 33 are oppositely positioned of each other along the third hose body 31. Additionally, the second attachment opening 32 and the fourth female quick connector 33 are in fluid communication with each other through the third hose body 31 thus providing a path for the flow of compressed warm air to travel into the heat exchanger 24. In reference to the connection points, the second attachment opening 32 is mounted to the male reservoir inlet 20 and positioned opposite of the output hose 14. In other words, the male reservoir inlet 20 functions as a coupler for the output hose 14 and the inlet connector hose 30 about the insulated reservoir 19. The fourth female quick connector 33 is attached to the air inlet 25. Resultantly, the flow of compressed warm air is respectively discharged from the male reservoir inlet 20 to the air inlet 25 through the second attachment opening 32, the third hose body 31, and the fourth female quick connector 33.

In reference to FIG. 5, the air outlet 27 is hermetically and releasably attached to the reservoir outlet 21 by the outlet connector hose 34, as the air outlet 27 and the reservoir outlet 21 are in fluid communication with each other by the outlet connector hose 34. As a result, the flow of compressed warm air that is emitted into the heat exchanger 24 through the inlet connector hose 30 is then discharged into the reservoir outlet 21 through the air outlet 27 and the outlet connector hose 34 as the flow of input cold air, respectively.

In reference to FIG. 5-6, the outlet connector hose 34 comprises a fourth hose body 35, a third attachment opening 36, and a fifth female quick connector 37. The third attachment opening 36 is terminally positioned within the fourth hose body 35 that is preferably made from flexible medical grade PVC or any other type of flexible biocompatible materials. The fifth female quick connector 37 is terminally mounted to the fourth hose body 35, opposite of the third attachment opening 36. In other words, the third attachment opening 36 and the fifth female quick connector 37 are oppositely positioned of each other along the fourth hose body 35. Additionally, the third attachment opening 36 and the fifth female quick connector 37 are in fluid communication with each other through the fourth hose body 35 thus providing a path for the flow of input cold air to travel from the heat exchanger 24. In reference to the connection points, the third attachment opening 36 is mounted to the reservoir outlet 21 and positioned opposite of the male air outlet 22 and the condensate drain outlet 23. In other words, the reservoir outlet 21 functions as a coupler for the male air outlet 22 and the outlet connector hose 34 about the insulated reservoir 19. The fifth female quick connector 37 is attached to the air outlet 27. Resultantly, the flow of input cold air is respectively discharged from the air outlet 27 to the reservoir outlet 21 through the third attachment opening 36, the fourth hose body 35, and the fifth female quick connector 37.

Figure 2:
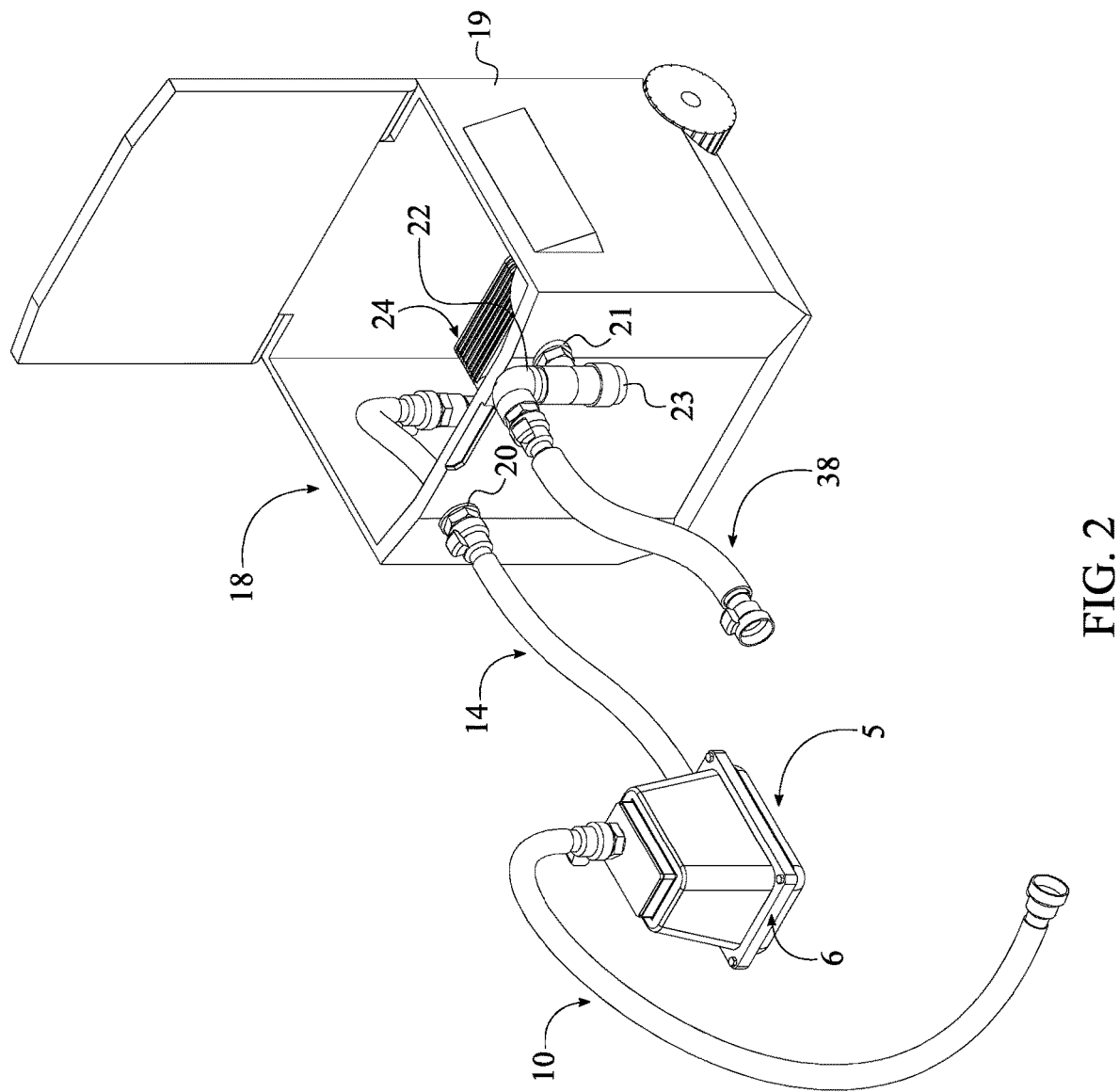
FIG. 2 is a top perspective view of the present invention, without the pressurized hyperbaric chamber.
Figure 3:
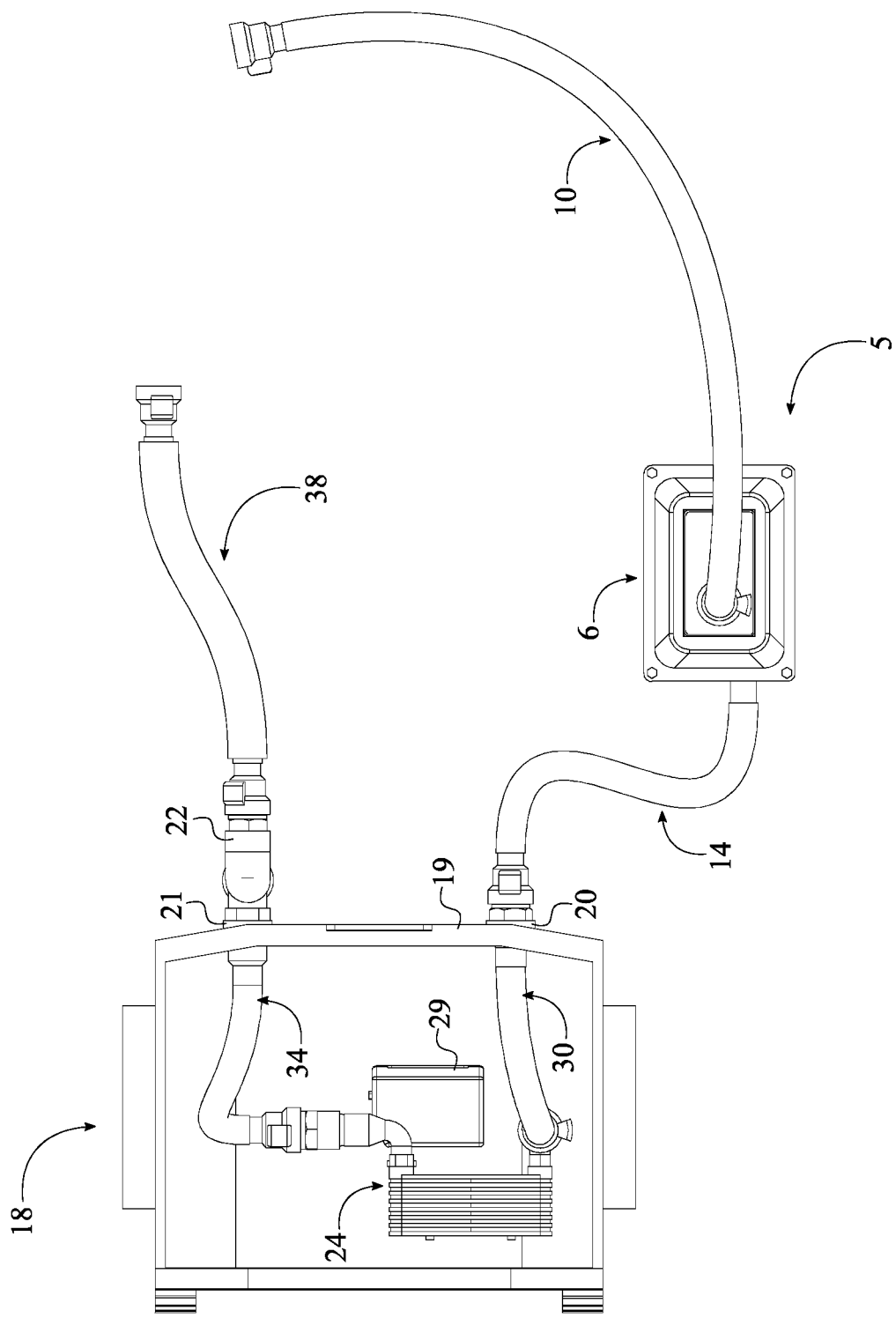
FIG. 3 is a top view of the present invention, without the pressurized hyperbaric chamber.

In reference to FIG. 1-3, the male air outlet 22 discharges the flow of input cold air from the air cooling unit 18. More specifically, the male air outlet 22 and the inlet male attachment 3 are hermetically and releasably attached to each other by the air discharging hose 38 as the male air outlet 22 and the inlet male attachment 3 are in fluid communication with each other by the air discharging hose 38. As a result, the flow of input cold air can be supplied to the pressurized hyperbaric chamber 1 through the air discharging hose 38. In order to maintain outputted temperature of the flow of input cold air, the length of the air discharging hose 38 is kept at minimum between the air cooling unit 18 and the pressurized hyperbaric chamber 1. Additionally, the air discharging hose 38 is also insulated to minimize heat absorption. The minimum length and insulation of the discharging hose 38 allow the present invention minimize heat absorption when the flow of input cold air travels from the air outlet 22 to the inlet male attachment 3.

Figure 7:
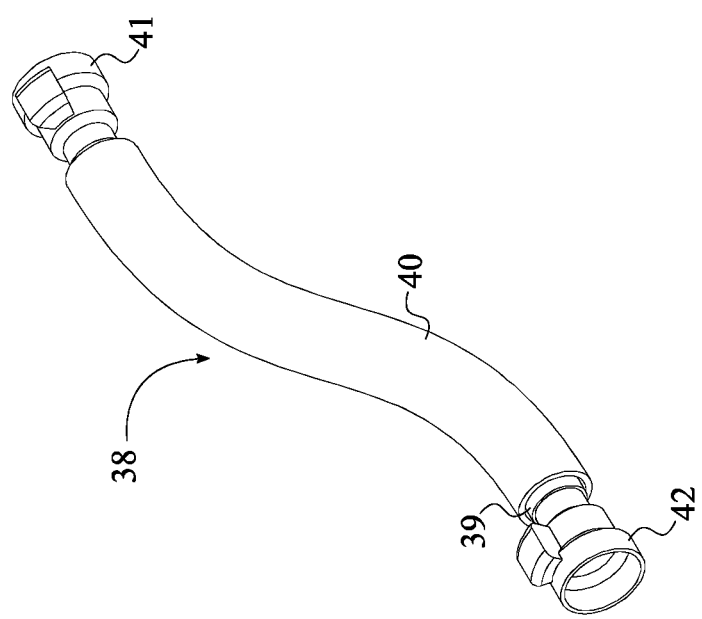
FIG. 7 is a perspective view of the air discharging hose of the present invention.

In reference to FIG. 7, the air discharging hose 38 comprises a fifth hose body 39, an insulated body 40, a sixth female quick connector 41, and a seventh female quick connector 42. The sixth female quick connector 41 is terminally mounted to the fifth hose body 39 that is preferably made from flexible medical grade PVC or any other type of flexible biocompatible materials. The seventh female quick connector 42 is terminally mounted to the fifth hose body 39, opposite of the sixth female quick connector 41. In other words, the sixth female quick connector 41 and the seventh female quick connector 42 are oppositely positioned of each other along the fifth hose body 39. Additionally, the sixth female quick connector 41 and the seventh female quick connector 42 are in fluid communication with each other through the fifth hose body 39 thus providing a path for the flow of input cold air to travel. The insulated body 40, which thermally protected the fifth hose body 39, is enclosed around the fifth hose body 39 in between the sixth female quick connector 41 and the seventh female quick connector 42. In reference to the connection points, the sixth female quick connector 41 is attached to the male air outlet 22, and the seventh female quick connector 42 is attached to the inlet male attachment 3. Resultantly, the flow of input cold air is respectively discharged from the male air outlet 22 to the pressurized hyperbaric chamber 1 through the sixth female quick connector 41, the fifth hose body 39, and the seventh female quick connector 42.

In reference to FIG. 2, the condensate drain outlet 23 collects and discharges any condensation that may build up during continuous operation of the present invention. The condensate drain outlet 23 is in fluid communication with the reservoir outlet 21 from one end and connected with a drain valve through an extension tube from the opposite end. The drain valve is kept at a closed positioned so that flow of input cold air is only existed through the air discharging hose 38. As a result, any condensation that may build up within the present invention is drained and collected within the extension tube due to gravitational force. By switching the closed position of the drain valve to an opened position, the drain valve allows the collected condensation to be drain out of the present invention.

Although the invention has been explained in relation to its preferred embodiment, it is to be understood that many other possible modifications and variations can be made without departing from the spirit and scope of the invention as hereinafter claimed.

What is claimed is:

1. A system for cooling a hyperbaric chamber without pressure change comprises:
   a pressurized hyperbaric chamber;
   an air compressing unit;
   an air cooling unit;
   an air discharging hose;
   the air cooling unit comprises an insulated reservoir, a male reservoir inlet, a reservoir outlet, a heat exchanger, and a submersible pump;

the heat exchanger comprises an air inlet, an air outlet, a water inlet, and a water outlet;
the pressurized hyperbaric chamber being in fluid communication with the air compressing unit;
the male reservoir inlet and the reservoir outlet traverses into the insulated reservoir;
the heat exchanger and the submersible pump being positioned within the insulated reservoir;
the air inlet being in fluid communication with the air compressing unit through the male reservoir inlet;
the water outlet being in fluid communication with the water inlet through the submersible pump;
the air outlet being in fluid communication with the air discharging hose through the reservoir outlet;
the pressurized hyperbaric chamber comprises a chamber body, an inlet male attachment, and an outlet male attachment;
the inlet male attachment and the outlet male attachment traverse into the chamber body; and
the inlet male attachment and the outlet male attachment being in fluid communication with the chamber body.

2. The system for cooling hyperbaric chamber without pressure change as claimed in claim 1 comprises:
the air compressing unit comprises a compressor, an input hose, and an output hose;
the compressor comprises a compressor body, a male air inlet, and a compressed air outlet;
the male air inlet and the compressed air outlet being in fluid communication with each other through the compressor body;
an outlet male attachment of the pressurized hyperbaric chamber and the male air inlet being hermetically and releasably attached to each other by the input hose;
the outlet male attachment and the male air inlet being in fluid communication with each other by the input hose;
the compressed air outlet and the male reservoir inlet being hermetically and releasably attached to each other by the output hose; and
the compressed air outlet and the male reservoir inlet being in fluid communication with each other by the output hose.

3. The system for cooling hyperbaric chamber without pressure change as claimed in claim 2 comprises:
the input hose comprises a first hose body, a first female quick connector, and a second female quick connector;
the first female quick connector being terminally mounted to the first hose body;
the second female quick connector being terminally mounted to the first hose body, opposite of the first female quick connector;
the first female quick connector and the second female quick connector being in fluid communication with each other through the first hose body;
the first female quick connector being attached to the outlet male attachment; and
the second female quick connector being attached to the male air inlet.

4. The system for cooling hyperbaric chamber without pressure change as claimed in claim 3 comprises:
the output hose comprises a second hose body, a first attachment opening, a third female quick connector;
the first attachment opening being terminally positioned within the second hose body;
the third female quick connector being terminally mounted to the second hose body, opposite of the first attachment opening;
the first attachment opening and the third female quick connector being in fluid communication with each other through the second hose body;
the first attachment opening being mounted to the compressed air outlet; and
the third female quick connector being attached to the male reservoir inlet.

5. The system for cooling hyperbaric chamber without pressure change as claimed in claim 4 comprises:
the air cooling unit further comprises an inlet connector hose, an outlet connector hose, a male air outlet, and a condensate drain outlet;
the inlet connector hose and the outlet connector hose being positioned within the insulated reservoir;
the male air outlet and the condensate drain outlet being positioned external to the insulated reservoir;
the male air outlet and the condensate drain outlet being connected to the reservoir outlet;
the air inlet being hermetically and releasably attached to the male reservoir inlet by the inlet connector hose;
the air inlet and the male reservoir inlet being in fluid communication with each other by the inlet connector hose;
the air outlet being hermetically and releasably attached to the reservoir outlet by the outlet connector hose; and
the air outlet and the reservoir outlet being in fluid communication with each other by the outlet connector hose.

6. The system for cooling hyperbaric chamber without pressure change as claimed in claim 5 comprises:
the inlet connector hose comprises a third hose body, a second attachment opening, a fourth female quick connector;
the second attachment opening being terminally positioned within the third hose body;
the fourth female quick connector being terminally mounted to the third hose body, opposite of the second attachment opening;
the second attachment opening and the fourth female quick connector being in fluid communication with each other through the third hose body;
the second attachment opening being mounted to the male reservoir inlet, opposite of the output hose; and
the fourth female quick connector being attached to the air inlet.

7. The system for cooling hyperbaric chamber without pressure change as claimed in claim 6 comprises:
the outlet connector hose comprises a fourth hose body, a third attachment opening, a fifth female quick connector;
the third attachment opening being terminally positioned within the fourth hose body;
the fifth female quick connector being terminally mounted to the fourth hose body, opposite of the third attachment opening;
the third attachment opening and the fifth female quick connector being in fluid communication with each other through the fourth hose body;
the third attachment opening being mounted to the reservoir outlet, opposite of the male air outlet and the condensate drain outlet; and
the fifth female quick connector being attached to the air outlet.

8. The system for cooling hyperbaric chamber without pressure change as claimed in claim 7 comprises:

the air discharging hose comprises a fifth hose body, an insulated body, a sixth female quick connector, and a seventh female quick connector;

the sixth female quick connector being terminally mounted to the fifth hose body;

the seventh female quick connector being terminally mounted to the fifth hose body, opposite of the sixth female quick connector;

the sixth female quick connector and the seventh female quick connector being in fluid communication with each other through the fifth hose body;

the fifth hose body being enclosed by the insulated body in between the sixth female quick connector and the seventh female quick connector;

the sixth female quick connector being attached to the male air outlet; and the seventh female quick connector being attached to the inlet male attachment.

9. The system for cooling hyperbaric chamber without pressure change as claimed in claim 1, the submersible pump being connected to the water inlet.

10. The system for cooling hyperbaric chamber without pressure change as claimed in claim 1 comprises:

a male air outlet of the air cooling unit and the inlet male attachment being hermetically and releasably attached to each other by the air discharging hose; and the male air outlet and the inlet male attachment being in fluid communication with each other by the air discharging hose.

\* \* \* \* \*